United States Patent
Robinson et al.

(10) Patent No.: US 8,470,932 B2
(45) Date of Patent: Jun. 25, 2013

(54) SCALABLE PROCESS FOR SYNTHESIS OF A CURABLE WAX

(75) Inventors: Sarah J. P. Robinson, Mississauga (CA); Thomas E. Enright, Tottenham (CA); Jennifer L. Belelie, Oakville (CA)

(73) Assignee: Xerox Corporation, Norwalk, CT (US)

( * ) Notice: Subject to any disclaimer, the term of this patent is extended or adjusted under 35 U.S.C. 154(b) by 527 days.

(21) Appl. No.: 12/756,415

(22) Filed: Apr. 8, 2010

(65) Prior Publication Data
US 2011/0247521 A1  Oct. 13, 2011

(51) Int. Cl.
*C08F 20/10* (2006.01)
*C08L 33/08* (2006.01)

(52) U.S. Cl.
USPC .......... 525/301; 525/50; 525/55; 525/242; 525/326.1; 106/271

(58) Field of Classification Search
USPC .......... 106/271; 525/301, 50, 55, 242, 326.1
See application file for complete search history.

(56) References Cited

U.S. PATENT DOCUMENTS

| 6,547,380 B2 | 4/2003 | Smith et al. |
| 7,559,639 B2 | 7/2009 | Belelie et al. |
| 2007/0120925 A1* | 5/2007 | Belelie et al. ............ 347/100 |
| 2009/0032989 A1* | 2/2009 | Karim et al. ............ 264/19 |

OTHER PUBLICATIONS

Chen, "Dimer Acids," Kirk-Othmer Encyclopedia of Chemical Technology, vol. 8, 4th Ed., pp. 223-237, 1992.
New U.S. Patent Application filed Apr. 8, 2010 in the name of Robinson et al.

* cited by examiner

*Primary Examiner* — Melissa Stalder
(74) *Attorney, Agent, or Firm* — Oliff & Berridge, PLC

(57) ABSTRACT

The methods of manufacturing a curable wax, such as an acrylate of a hydroxyl-terminated polyethylene wax having the structure $CH_3$—$(CH_2)_n$—$CH_2OH$, where n=22-24, are disclosed. The methods may include reacting a wax having a transformable functional group and a curable compound in the presence of an organic solvent to form an acrylate. The methods may further include removing excess curable compound using hot water having a temperature of more than 85° C., and solidifying the acrylate. The methods may thereby provide safe and cost effective methods for curable wax production at large scale.

18 Claims, No Drawings

SCALABLE PROCESS FOR SYNTHESIS OF A CURABLE WAX

TECHNICAL FIELD

Described herein are methods of synthesizing curable wax, particularly a hydroxyl-terminated polyethylene wax acrylate, for use in the formation of radiation curable inks.

RELATED APPLICATIONS

In application Ser. No. 11/289,615 (entitled "Radiation Curable Ink Containing a Curable Wax," Jennifer L. Belelie et al.), filed Nov. 30, 2005, now U.S. Pat. No. 7,559,639 described is a method of preparing a curable wax in the presence of toluene.

U.S. patent application Ser. No. 12/756,250, filed Apr. 8, 2010, now U.S. Pat. No. 8,207,274, the disclosure of which is hereby incorporated by reference in its entirety, describes a method of manufacturing a curable wax that comprises reacting in a reactor a wax having a transformable functional group and a curable compound in the absence of an organic solvent to form an acrylate, removing water and excess curable compound, solidifying the acrylate, removing the acrylate from the reactor, and removing a fouled material from the reactor by emulsification.

BACKGROUND

While methods of synthesizing curable wax have been successful at small production scale, improved processes providing safe and cost effective methods for curable wax production at large scale are desirable. Specifically, methods that use less organic solvent while achieving increased throughput are desirable. Methods that discharge the bottom fraction of the product into methanol result in an increase in the average molecular weight (and therefore melting point) of the sample. A higher melting point for the acrylated product results in slower filtration times in the final ink. Methods that have improved (faster) filtration times are desirable.

SUMMARY

In embodiments, described is a method of manufacturing a curable wax, the method comprising reacting a wax having a transformable functional group and a curable compound in the presence of an organic solvent to form an acrylate, removing water and excess curable compound using hot water having a temperature of more than about 85° C., and solidifying the acrylate using cold water and/or an alcohol having a temperature of less than about 10° C.

Also described is a method of manufacturing a curable wax, the method comprising reacting a wax having a transformable functional group and a curable compound in the presence of an organic solvent to form an acrylate, where the wax having a transformable functional group is a hydroxyl-terminated polyethylene wax having the structure $CH_3$—$(CH_2)_n$—$CH_2OH$, where n=22-24, and the curable compound is an acrylic acid, removing water and excess curable compound using hot water having a temperature of more than about 90° C., and solidifying the acrylate using cold water and/or an alcohol having a temperature of less than about 10° C.

Still further described is a method of manufacturing a curable wax, the method comprising reacting a wax having a transformable functional group and a curable compound in the presence of an organic solvent to form an acrylate, removing water and excess curable compound using hot water having a temperature of more than about 85° C., where removing water and excess curable compound is performed by at least one extraction process using hot water, the extraction process comprising removing the excess curable compound from a waxy phase into a water phase, and removing the water phase, and solidifying the acrylate using cold water and/or an alcohol having a temperature of less than about 10° C.

Yet further described is a method of manufacturing a radiation curable ink, the method comprising providing a curable monomer, providing a colorant, and providing a curable wax, where the curable wax is formed by a reaction between a wax having a transformable functional group and a curable compound, where the reaction occurs in the presence of an organic solvent in an amount of about 24 wt % to about 48%.

Even further described is a radiation curable ink comprising a curable monomer, a colorant, and a curable wax formed by reacting a wax having a transformable functional group and a curable compound in the presence of an organic solvent to form an acrylate, removing water and excess curable compound using hot water having a temperature of more than about 90° C., and solidifying the acrylate using cold water and/or an alcohol having a temperature of less than about 10° C.

DETAILED DESCRIPTION OF EMBODIMENTS

Described are methods of synthesizing a curable wax, such as an acrylate of a hydroxyl-terminated polyethylene wax having the structure $CH_3$—$(CH_2)_n$—$CH_2OH$, where n=22-24, in a scaleable process by using less organic solvent than in conventional processes, and purifying the curable wax product by using water in place of an organic solvent. Such methods provide several advantages, including reduction of organic solvent used in the synthesis process, resulting in an increase in reactor throughput, and significant safety and cost improvement as a result of using water in place of organic solvents, such as methanol, during purification and isolation of the curable wax. The use of water during purification and isolation further provides the advantage of reduced amount of fractionation and improved product characteristics, including the melting point of the curable wax. In addition to improved (lower) melting points in the product, filtration times are also improved (faster). The method herein is a scaleable process that is suitable for manufacturing curable wax. Other advantages will be apparent from the description herein.

The process of synthesizing the curable wax involves a condensation reaction between a wax having a transformable functional group and a curable compound. For example, the process may involve reacting a wax having a transformable functional group and a curable compound in the presence of toluene sulphonic acid, hydroquinone and an organic solvent, in a heated environment to form an acrylate, cooling the acrylate, removing water and excess curable compound, and solidifying the acrylate. During the reaction, water condensate and toluene distillate may be collected by a condenser.

Suitable examples of waxes include those that are functionalized acrylate and/or methacrylate groups. These waxes can be synthesized by the reaction of a wax equipped with a transformable functional group, such as carboxylic acid or hydroxyl, with a compound that provides the curable group.

Suitable examples of hydroxyl-terminated polyethylene waxes that may be functionalized with a curable group include, but are not limited to, mixtures of carbon chains with the structure $CH_3$—$(CH_2)_{n-CH2}OH$, where there is a mixture of chain lengths, n, where the average chain length is, for example, in the range of about 16 to about 50, such as about 20 to about 30 or about 40, and linear low molecular weight polyethylene, of similar average chain length. Suitable examples of such waxes include, but are not limited to, UNILIN® 350, UNILIN® 425 and UNILIN® 550 with $M_n$ approximately equal to 375, 460, and 550 g/mol, respectively. All of these waxes are commercially available from Baker-Petrolite. Guerbet alcohols, characterized as 2,2-dialkyl-1-ethanols, are also suitable compounds. Suitable examples of Guerbet alcohols include those containing 16 to 36 carbons, many of which are commercially available from Jarchem Industries Inc., Newark, N.J. PRIPOL® 2033 (C-36 dimer diol mixture including isomers of the formula

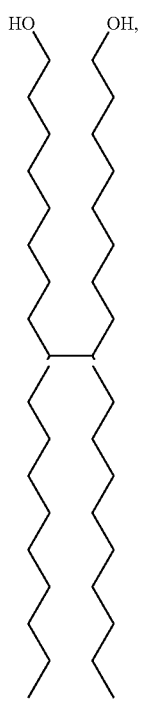

as well as other branched isomers which may include unsaturations and cyclic groups, available from Uniqema, New Castle, Del.; further information on $C_{36}$ dimer diols of this type is disclosed in, for example, "Dimer Acids," *Kirk-Othmer Encyclopedia of Chemical Technology*, Vol. $4^{th}$ Ed. (1992), pp. 223 to 237, the disclosure of which is totally incorporated herein by reference) can also be used. These alcohols can be reacted with carboxylic acids equipped with UV curable moieties to form reactive esters. Examples of these acids include, but are not limited to, acrylic and methacrylic acids, available from Sigma-Aldrich Co. In embodiments, the reaction product in the form of curable monomers may be acrylates of UNILIN® 350, UNILIN® 425, UNILIN® 550.

In embodiments, the process involves reacting a hydroxyl-terminated polyethylene wax, such as a wax having the structure $CH_3-(CH_2)_n-CH_2OH$, where n=22-24, and an acrylic acid in the presence of toluene sulphonic acid and hydroquinone and an organic solvent, in a heated environment to form an acrylate, cooling the acrylate, removing water and excess acrylic acid, and solidifying the acrylate. This reaction is illustrated by the following formula:

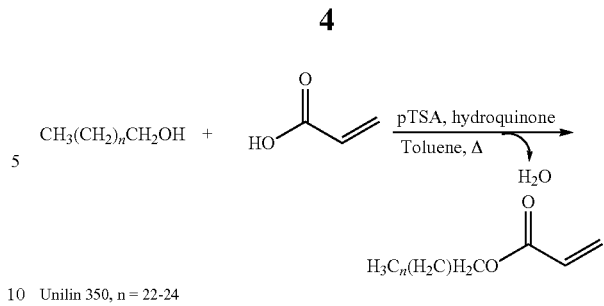

Unilin 350, n = 22-24

A suitable organic solvent may be toluene, hexane, benzene, ethyl acetate, 1,4-dioxane, dichloromethane (DCM), acetonitrile (MeCN), dimethylformamide (DMF), and dimethyl sulfoxide (DMSO). The organic solvent used in the process may be included in an amount from about 12 to about 36% by weight. In embodiments, the amount may be from about 18 to about 30% by weight or about 20 to about 28% by weight. In other embodiments, the amount may be from about 12 to about 24% by weight or about 24 to about 36% by weight, such as from about 18 to about 24% or from about 24 to about 30%.

Compounds such as p-toluene sulfonic acid (as a catalyst) and hydroquinone (as a radical trap) may be added to the reaction. Other catalysts may include sulfuric acid, methyl sulfonic acid, ethyl sulfonic acid, propyl sulfonic acid, and hydrochloric acid. Other radical traps may include hydroquinone mono methyl ether, p-(naphthyl-1-methoxy)phenol, p-(naphthyl-2-methyoxy)phenol, 2-(naphthyl-1-methyl)hydroquinone, 2-(naphthyl-1-methyl)-1,4-benzoquinone, o-xylylene-bis-hydroquinone ether, m-xylylene-bis-hydroquinone ether, p-xylylene-bis-hydroquinone ether, hydroquinone(4-phenoxymethyl)benzyl ether, 2,5-bis (napthyl-1-methyl)hydroquinone, 1-(3,4-dihydroxybenzyl)naphthalene, 2,5-dibenzylhydroquinone, 4-benzyloxy-2-benzylphenol, 2,5-dibenzyl-1,4-benzoquinone, 3-(naphthyl-1-methyl)-1,2-benzoquinone, 2,6-di-t-butyl-4-(naphthyl-1-methoxy)phenol, phenothiazine, t-butylcatechol, p-benzoquinone, methylene blue, diphenylamine, and 4-hydroxy-2,2,6,6-tetramethylpiperidinooxyl.

The step of removing water and excess curable compound may involve at least one extraction process using hot water, the extraction process comprising removing the excess curable compound from a waxy phase into a water phase, and removing the water phase. In other embodiments, the extraction process may be repeated two, three or more times. In embodiments, during the last extraction process, the water phase is not removed such that the water phase serves to preheat the discharge line to a vacuum filter for isolating the acrylate.

The hot water used for the extraction process may have a temperature of more than about 85° C., such as from about 90 to about 100° C.

The acrylate may be solidified by adding the acrylate to cold water such that the acrylate becomes solid, isolating the solid acrylate by filtration, and drying the solid acrylate. The cold water may have a temperature of less than 10° C. The acrylate may also be discharged to an alcohol (having a temperature of less than 10° C.), such as isopropanol or methanol, or a mixture of these solvents and water (having a temperature of less than 10° C.). These cooling methods form discrete particles. Another cooling method that may be used involves separating the final water phase to a pail and discharging the waxy (product) phase to trays, and allowing the material to cool slowly at room temperature. This method may then require physical breaking of the solid waxy "sheets." Filtration may be performed by any known filtration methods, including the use of a vacuum filter. Drying the solid acrylate may also be performed by any known drying method, including the use of a vacuum oven. Drying may be performed at a temperature of 70° C. or less, such as 60° C.; but should not be carried out at more than 70° C. to avoid melting the product and/or fusing the product back together (negating the advantage to previously forming discrete particles).

Agitation of the reactor may be utilized to stir the solution during reaction and extraction. Any suitable stirring (agitation) device may be utilized. The stirring need not be at a constant speed, but may be varied. The stirring may be at from about 10 revolutions per minute (rpm) to about 300 rpm. In embodiments, the stirring may be from about 50 to about 250 rpm or from about 100 to about 150 rpm. In other embodiments, the stirring may be from about 10 to about 150 rpm or from about 200 to about 300 rpm.

As noted above, the curable wax formed by the present method may be used in forming radiation curable ink. An exemplary composition of radiation curable inks is described in co-pending application Ser. No. 11/289,615, the entire disclosure of which is incorporated herein by reference.

As described in co-pending application Ser. No. 11/289,615, the radiation curable ink, in embodiments, comprises a curable monomer that is liquid at about 25° C., a curable wax, and a colorant. In embodiments, the curable monomer has a viscosity of no more than about 20 mPa-s, in other embodiments no more than about 18 mPa-s, and yet in other embodiments no more than about 16 mPa-s at about 25° C.

In embodiments, the ink has a viscosity of from about 8 mPa-s to about 15 mPa-s, in other embodiments from about 10 mPa-s to about 12 mPa-s, at a temperature between about 60° C. and about 100° C. In embodiments, the ink has a viscosity of from about $10^5$ to about $10^7$ mPa-s at a temperature of about 50° C. or below, specifically at a temperature from about 0° C. to about 50° C.

The curable monomer may be any curable monomer that is a liquid at about 25° C. In embodiments, the monomer is equipped with one or more curable moieties, including, but not limited to, acrylates; methacrylates; alkenes; allylic ethers; vinyl ethers; epoxides, such as cycloaliphatic epoxides, aliphatic epoxides, and glycidyl epoxides; oxetanes; and the like. The monomers are, for example, monoacrylates, diacrylates, or polyfunctional alkoxylated or polyalkoxylated acrylic monomers comprising one or more di- or tri-acrylates.

Suitable monoacrylates are, for example, cyclohexyl acrylate, 2-ethoxy ethyl acrylate, 2-methoxy ethyl acrylate, 2-(2-ethoxyethoxy)ethyl acrylate, tetrahydrofurfuryl acrylate, octyl acrylate, lauryl acrylate, 2-phenoxy ethyl acrylate, tertiary butyl acrylate, glycidyl acrylate, isodecyl acrylate, benzyl acrylate, hexyl acrylate, isooctyl acrylate, isobornyl acrylate, butanediol monoacrylate, octyl decyl acrylate, ethoxylated nonylphenol acrylate, hydroxyethyl acrylate, hydroxyethyl methacrylate, and the like. Suitable polyfunctional alkoxylated or polyalkoxylated acrylates are, for example, alkoxylated, in embodiments, ethoxylated, or propoxylated, variants of the following: neopentyl glycol diacrylates, butanediol diacrylates, 1,3-butylene glycol diacrylate, 1,4-butanediol diacrylate, diethylene glycol diacrylate, 1,6-hexanediol diacrylate, tetraethylene glycol diacrylate, triethylene glycol diacrylate, tripropylene glycol diacrylate, propoxylated neopentyl glycol diacrylate, ethoxylated neopentyl glycol diacrylate, and the like. In embodiments, the monomer is a propoxylated neopentyl glycol diacrylate, such as, for example, SR-9003 (Sartomer Co., Inc., Exton, Pa.), having the structure:

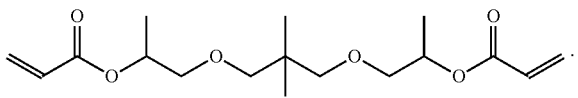 [SMILES: C=CC(=O)OC(C)COCC(C)(C)COCC(C)OC(=O)C=C]

Suitable reactive monomers are likewise commercially available from, for example, Sartomer Co., Inc., Henkel Corp., Radcure Specialties, and the like.

In embodiments, the curable monomer is included in the ink in an amount of from, for example, about 20 to about 80% by weight of the ink, specifically from about 30 to about 70% by weight of the ink, and more specifically from about 35 to about 60% by weight of the ink.

In other embodiments, the curable wax is included in the ink in an amount of from, for example, about 15 to about 70% by weight of the ink, specifically from about 20 to about 60% by weight of the ink, and more specifically from about 25 to about 50% by weight of the ink.

The curable monomer and curable wax together, for example, form more than about 50% by weight of the ink, specifically at least about 70% by weight of the ink, and more specifically at least about 80% by weight of the ink. The weight ratio of curable monomer to curable wax may be, for example, from about 0.7:1 to about 3:1, specifically from about 0.75:1 to about 2.5:1.

Any desired or effective colorant can be employed in the inks, including dyes, pigments, mixtures thereof, and the like, provided that the colorant can be dissolved or dispersed in the ink vehicle. The compositions can be used in combination with conventional ink colorant materials, such as Color Index (C.I.) Solvent Dyes, Disperse Dyes, modified Acid and Direct Dyes, Basic Dyes, Sulphur Dyes, Vat Dyes, and the like.

Examples of suitable dyes include, but are not limited to, Eastman olefin, Usharect Blue 86 (Direct Blue 86), available from Ushanti Color; Intralite Turquoise 8GL (Direct Blue 86), available from Classic Dyestuffs; Chemictive Brilliant Red 7BH (Reactive Red 4), available from Chemiequip; Levafix Black EB, available from Bayer; Reactron Red H8B (Reactive Red 31), available from Atlas Dye-Chem; D&C Red #28 (Acid Red 92), available from Warner-Jenkinson; Direct Brilliant Pink B, available from Global Colors; Acid Tartrazine, available from Metrochem Industries; Cartasol Yellow 6GF Clariant; Carta Blue 2GL, available from Clariant; and the like. In embodiments, solvent dyes are used; within the class of solvent dyes, spirit soluble dyes may be used because of their compatibility with the ink vehicles of the present invention. Examples of suitable spirit solvent dyes include Neozapon Red 492 (BASF); Orasol Red G (Ciba); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (Ciba); Orasol Black RLP (Ciba); Savinyl Black RLS (Clariant); Morfast Black Conc. A (Rohm and Haas); Orasol Blue GN (Ciba); Savinyl Blue GLS (Sandoz); Luxol Fast Blue MBSN (Pylam); Sevron Blue 5GMF (Classic Dyestuffs); Basacid Blue 750 (BASF), and the like. Neozapon Black X51 [C.I. Solvent Black, C.I. 12195] (BASF), Sudan Blue 670 [C.I. 61554] (BASF), Sudan Yellow 146 [C.I. 12700] (BASF), and Sudan Red 462 [C.I. 260501] (BASF) may also be used.

Pigments are also suitable colorants for the inks. Examples of suitable pigments include, but are not limited to, Violet PALIOGEN Violet 5100 (BASF); PALIOGEN Violet 5890 (BASF); HELIOGEN Green L8730 (BASF); LITHOL Scarlet D3700 (BASF); Sunfast® Blue 15:4 (Sun Chemical 249-0592); Hostaperm Blue B2G-D (Clariant); Permanent Red P-F7RK; Hostaperm Violet BL (Clariant); LITHOL Scarlet 4440 (BASF); Bon Red C (Dominion Color Company); ORACET Pink RF (Ciba); PALIOGEN Red 3871 K (BASF); Sunfast® Blue 15:3 (Sun Chemical 249-1284); PALIOGEN Red 3340 (BASF); Sunfast® Carbazole Violet 23 (Sun Chemical 246-1670); LITHOL Fast Scarlet L4300 (BASF); Sunbrite Yellow 17 (Sun Chemical 275-0023); HELIOGEN Blue L6900, L7020 (BASF); Sunbrite Yellow 74 (Sun Chemical 272-0558); Spectra Pac® C Orange 16 (Sun Chemical 276-3016); HELIOGEN Blue K6902, K6910 (BASF); Sunfast® Magenta 122 (Sun Chemical 228-0013); HELIOGEN Blue D6840, D7080 (BASF); Sudan Blue OS (BASF); NEOPEN Blue FF4012 (BASF); PV Fast Blue B2GO1 (Clariant); IRGALITE Blue BCA (Ciba); PALIOGEN Blue 6470 (BASF); Sudan Orange G (Aldrich), Sudan Orange 220 (BASF); PALIOGEN Orange 3040 (BASF); PALIOGEN Yellow 152, 1560 (BASF); LITHOL Fast Yellow 0991 K (BASF); PALIOTOL Yellow 1840 (BASF); NOVOPERM Yellow FGL (Clariant); Lumogen Yellow D0790 (BASF); Suco-Yellow L1250 (BASF); Suco-Yellow D1355 (BASF); Suco Fast Yellow D1 355, D1 351 (BASF); HOSTAPERM Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA Magenta (DU PONT), PALIOGEN Black L0084 (BASF); Pigment Black K801 (BASF); and carbon blacks such as REGAL 330™. (Cabot), Carbon Black 5250, Carbon Black 5750 (Columbia Chemical), mixtures thereof and the like.

In embodiments, the colorant is included in the ink in an amount of from, for example, about 0.1 to about 15% by weight of the ink, specifically from about 0.5 to about 6% by weight of the ink.

Radiation curable as used herein is intended to cover all forms of curing upon exposure to a radiation source, including light and heat sources and including in the presence or absence of initiators. Example radiation curing routes include, but are not limited to, curing using ultraviolet (UV) light, for example having a wavelength of 200-400 nm or more rarely visible light, for example in the presence of photoinitiators and/or sensitizers, curing using e-beam radiation, for example in the absence of photoinitiators, curing using thermal curing, in the presence or absence of high temperature thermal initiators (and which may be largely inactive at the jetting temperature), and appropriate combinations thereof.

In embodiments, the composition further comprises an initiator, such as a photoinitiator, that initiates polymerization of curable components of the ink, including the curable monomer and the curable wax. The initiator should be soluble in the composition. In other embodiments, the initiator is a UV-activated photoinitiator.

In embodiments, the initiator is a radical initiator. Examples of suitable radical photoinitiators include, but are not limited to, ketones such as benzyl ketones, monomeric hydroxyl ketones, polymeric hydroxyl ketones, and α-amino ketones; acyl phosphine oxides, metallocenes, benzophenones, such as 2,4,6-trimethylbenzophenone and 4-methylbenzophenone; and thioxanthenones, such as 2-isopropyl-9H-thioxanthen-9-one. A suitable ketone is 1-[4-(2-hydroxyethoxy)-phenyl]-2-hydroxy-2-methyl-1-propane-1-one. In embodiments, the ink contains an α-amino ketone, 1-[4-(2-hydroxyethoxy)-phenyl]-2-hydroxy-2-methyl-1-propane-1-one and 2-isopropyl-9H-thioxanthen-9-one.

In other embodiments, the initiator is a cationic initiator. Examples of suitable cationic photoinitiators include, but are not limited to, aryldiazonium salts, diaryliodonium salts, triarysulfonium salts, triarylselenonium salts, dialkylphenacylsulfonium salts, triarylsulphoxonium salts and aryloxydiarylsulfonium salts.

The total amount of initiator included in the ink may be from, for example, about 0.5 to about 15%, specifically from about 1 to about 10%, by weight of the ink.

In embodiments, the ink further comprises a curable oligomer. Suitable curable oligomers include, but are not limited to, acrylated polyesters, acrylated polyethers, acrylated epoxies, urethane acrylates, and pentaerythritol tetraacrylate. Specific examples of suitable acrylated oligomers include, but are not limited to, acrylated polyester oligomers, such as CN2262 (Sartomer Co.), EB 812 (UCB Chemicals), CN2200 (Sartomer Co.), CN2300 (Sartomer Co.), and the like, acrylated urethane oligomers, such as EB270 (UCB Chemicals), EB 5129 (UCB Chemicals), CN2920 (Sartomer Co.), CN3211 (Sartomer Co.), and the like, acrylated epoxy oligomers, such as EB 600 (UCB Chemicals), EB 3411 (UCB Chemicals), CN2204 (Sartomer Co.), CN110 (Sartomer Co.), and the like; and pentaerythritol tetraacrylate oligomers, such as SR399LV (Sartomer Co.) and the like.

The total amount of curable oligomer included in the ink may be, for example, about 0.5 to about 15%, specifically about 1 to about 10%, by weight of the ink.

The ink may contain optional additives. Optional additives include, but are not limited to, surfactants, light stabilizers, UV absorbers, which absorb incident UV radiation and convert it to heat energy that is ultimately dissipated, antioxidants, optical brighteners, which can improve the appearance of the image and mask yellowing, thixotropic agents, dewetting agents, slip agents, foaming agents, antifoaming agents, flow agents, waxes, oils, plasticizers, binders, electrical conductive agents, fungicides, bactericides, organic and/or inorganic filler particles, leveling agents, e.g., agents that create or reduce different gloss levels, opacifiers, antistatic agents, dispersants, and the like. In particular, the composition may include, as a stabilizer, a radical scavenger, such as Irgastab UV 10 (Ciba Specialty Chemicals, Inc.). The composition may also include an inhibitor, such as a hydroquinone, to stabilize the composition by prohibiting or, at least, delaying, polymerization of the oligomer and monomer components during storage, thus increasing the shelf life of the composition. However, additives may negatively affect cure rate, and thus care must be taken when formulating a composition using optional additives.

The total amount of other additives included in the ink may be from, for example, about 0.5 to about 15%, specifically from about 1 to about 10%, by weight of the ink.

The inks described herein may be applied to a substrate to form an image. In embodiments, the method comprises providing a radiation curable ink described herein at a first temperature; applying the radiation curable ink to the substrate to form an image, the substrate being at a second temperature, which is below the first temperature; and exposing the radiation curable ink to radiation to cure the ink. During the curing process, the curable monomer and the curable wax, optionally with other curable components, such as the optional curable oligomer, are polymerized to form a cured image.

In embodiments, the composition is applied over the image by ink jet printing. The inks described herein may be jetted at temperatures of about 50° C. to about 110° C., specifically about 60° C. to about 100° C. The jetting temperature must be within the range of thermal stability of the composition, to prevent premature polymerization in the print head. At jetting, the inks in embodiments have a viscosity of from about 8 mPa-s to about 15 mPa-s, specifically about 10 mPa-s to about 12 mPa-s. The inks are thus ideally suited for use in piezoelectric ink jet devices.

However, the substrate to which they are applied could be at a temperature at which the ink has a higher viscosity, such as a viscosity of from about $10^5$ to about $10^7$ mPa-s. For example, the substrate may be maintained at a temperature of about 50° C. or below, specifically from about 0° C. to about 50° C., the temperature at the substrate being less than the jetting temperature. In embodiments, the substrate temperature is at least about 10° C. below the first temperature. In other embodiments, the substrate temperature is from about 10 to about 50° C. below the jetting temperature.

By jetting the ink at a temperature at which the ink is a liquid and having the substrate at the temperature at which the ink has a higher viscosity, a phase change can be provided. This phase change may prevent the composition from rapidly soaking into the substrate, avoiding or at least minimizing showthrough. In addition, the substrate is exposed to radiation to initiate polymerization of the curable monomer and curable wax, leading to a robust image.

The inks can be employed in apparatus for direct printing ink jet processes, where when droplets of the melted ink are ejected in an imagewise pattern onto a recording substrate, the recording substrate is a final recording substrate. Alternatively, the inks can be employed in indirect (offset) printing ink jet applications, where when droplets of the melted ink are ejected in an imagewise pattern onto a recording substrate, the recording substrate is an intermediate transfer member and the ink in the imagewise pattern is subsequently transferred from the intermediate transfer member to a final recording substrate. In both cases, the image on the substrate is exposed to UV light to initiate polymerization of the curable monomer and curable wax to form a robust image.

The substrate may be any suitable material such as paper, boxboard, cardboard, fabric, a transparency, plastic, glass, wood etc., although the ink may be used in forming images on paper. Following printing directly to or transfer to the substrate, the image on the substrate is exposed to radiation having an appropriate wavelength, mainly the wavelength at which the ink initiator absorbs radiation, to initiate the curing reaction of the ink. The radiation exposure need not be long, and may be for, e.g., about 0.05 to about 10 seconds, specifically from about 0.2 to about 5 seconds. These exposure times are more often expressed as substrate speeds of the ink passing under a UV lamp. For example, the microwave energized, doped mercury bulbs available from UV Fusion (Gaithersburg, Md.) are placed in an elliptical mirror assembly that is 10 cm wide; multiple units may be placed in series. Thus, a belt speed of 0.1 ms$^{-1}$ would require 1 second for a point of an image to pass under a single unit, while a belt speed 4.0 ms$^{-1}$ would require 0.2 s to pass under four bulb assemblies. The radiation to cure the polymerizable components of the ink may be provided by a variety of possible techniques, including but not limited to a xenon lamp, laser light, D or H bulb, etc. The curing light may be filtered, if desired or necessary. The curable components of the ink react to form a cured or crosslinked network of appropriate hardness. In embodiments, the curing is substantially complete, i.e., at least about 75% of the curable components are cured (polymerized and/or crosslinked), to allow the ink to be substantially hardened, and thereby to be much more scratch resistant, and also to adequately control the amount of showthrough on the substrate.

The present disclosure is also directed to a printer containing the inks described herein. Specifically, the present disclosure relates to a printer cartridge containing the inks described herein, as well as to a printer containing the printer cartridge.

In embodiments, the curable wax formed from the present disclosure may be used in ink jetting devices. Ink jetting devices are known in the art, and thus extensive description of such devices is not required herein. As described in U.S. Pat. No. 6,547,380, incorporated herein by reference, ink jet printing systems generally are of two types: continuous stream and drop-on-demand.

In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a substrate. In drop-on-demand systems, a droplet is expelled from an orifice directly to a position on a substrate in accordance with digital data signals. A droplet is not formed or expelled unless it is to be placed on the substrate.

There are at least three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

An example is set forth hereinbelow and is illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLE 1

Synthesis of UNILIN® 350 Acrylate at 5 Gal Scale 5.4 kg of UNILIN® 350, 6.8 g of hydroquinone, 53.5 g of p-toluene sulfonic acid and 1.1 kg of toluene were charged through the charge port into a reactor. The charge port was closed and the reactor was heated to a jacket temperature of 120° C. Agitation was begun at minimum once the reactor contents reached a temperature of approximately 65° C. Once the internal reactor temperature reached 85° C., signaling that the solids have melted, agitation was increased to 150 rpm. The final two reagents were added via a Pope tank. First, 1.32 kg of Acrylic Acid was added, and then Pope tank and lines were rinsed through the reactor with 1.1 kg of toluene. The time of acrylic acid addition was marked as time zero. The jacket temperature was then ramped from 120° C. to 145° C. over 120 minutes. This was done manually with an increase of 2° C. every 10 minutes as System Six program generator does not have the capability of ramping jacket temperatures. During this time, reaction condensate (water) was cooled and collected by a condenser. Approximately 200 g of water was collected. Also, approximately 1.1 kg of toluene (50% of the charge) was removed by distillation along with the reaction condensate.

Once the reactor jacket reached the maximum temperature of 145° C., cooling was begun to bring the reactor to a batch temperature of 95° C. Agitation was reduced to 115 rpm. 2.7 kg of de-ionized water ("DIW") was brought to boil and then charged to the reactor via the Pope tank (temperature of water by the time of transfer was greater than 90° C.). Mixing continued for 30 seconds and, after mixing was stopped, the water and waxy acrylate phases were allowed to separate. The bottom (water) phase was discharged to a steel pail from the bottom valve, using the sight-glass to monitor for the interface. The extraction procedure was repeated with another 2.7 kg of hot DIW, separated and the water discharged to a pail. A third and final extraction was conducted with 10 kg of hot DIW, separated but not discharged to a pail. Instead, this hot water layer was used to preheat the discharge line to a vacuum filter.

At the start of the experiment day, preparations were made to a vacuum filter for the discharge and precipitation steps. The filter was charged with 100 kg of DIW. Domestic cold water cooling and agitation at minimum was begun to the jacket of the filter to facilitate cooling the DIW to less than 10° C. for product solidification.

Following the third extraction, maximum agitation was begun to the filter (this agitator was not equipped with a tachometer). The reactor, the filter and the discharge lines were all checked for proper bonding and grounding, and both vessels were purged with nitrogen to ensure an inert atmosphere. The reactor was isolated, and a moderate (10 SCFH) nitrogen blanket on the filter was begun, and was maintained throughout the discharge procedure.

After the final 10 minutes of separation time, and once $T_r$=95° C., 5 kPa of nitrogen pressure was applied to the reactor. This ensured an inert atmosphere throughout the discharge procedure. The bottom valve was opened slightly and the hot reactor contents were slowly poured into the filter. The first layer was water, and the next layer, the desired UNILIN 350 acrylate, solidified into yellowish white particles. Once the discharge was complete, all nitrogen purges was stopped and both vessels vented to the atmosphere. Agitation continued on the filter for approximately 10 minutes. A flexible transfer line was connected from the central vacuum system to a waste receiver. Full vacuum was applied to the waste receiver, then the bottom valve of the filter was opened to vacuum transfer the water filtrate.

Once a dried sample of the material had an acid number of <1.5, the batch was discharged by hand into foil lined trays, and dried in a vacuum oven at 55° C. with full vacuum overnight. The next day, the dry material was discharged and stored in 5 gallon pails. The yield from the batch was approximately 5.2 kg.

What is claimed is:

1. A method of manufacturing a curable wax, the method comprising:
   reacting a wax having a transformable functional group and a curable compound in the presence of an organic solvent to form curable wax, removing excess curable compound using hot water having a temperature of more than about 85° C., and solidifying the curable wax, wherein the removing excess curable compound is performed by at least one extraction process using hot water, the extraction process comprising:
   removing the excess curable compound from a waxy phase into a water phase, and
   removing the water phase.

2. The method of claim 1, wherein the hot water has a temperature of from about 85° C. to about 100° C.

3. The method of claim 1, wherein the organic solvent is in an amount of from about 12 wt % to about 36 wt %.

4. The method of claim 1, wherein solidifying the curable wax comprises using cold water, an alcohol, or mixtures thereof having a temperature of less than about 10° C.

5. The method of claim 1, wherein the organic solvent is toluene.

6. The method of claim 1, wherein the transformable functional group is a carboxylic acid or a hydroxyl group.

7. The method of claim 1, wherein the wax having a transformable functional group is a hydroxyl-terminated polyethylene wax.

8. The method of claim 1, wherein the wax having a transformable functional group is a hydroxyl-terminated polyethylene wax having the structure $CH_3-(CH_2)_n-CH_2OH$, wherein n=22-24.

9. The method of claim 1, wherein the curable compound comprises a curable group selected from the group consisting of acrylate and methacrylate.

10. The method of claim 1, wherein the curable compound is an acrylic acid.

11. The method of claim 1, wherein the wax having a transformable functional group is a hydroxyl-terminated polyethylene wax having the structure $CH_3-(CH_2)_n-CH_2OH$, wherein n=22-24, and the curable compound is an acrylic acid.

12. The method of claim 1, wherein the extraction process is performed at least 3 times.

13. The method of claim 12, wherein the water phase is not removed during a last extraction process.

14. The method of claim 1, wherein solidifying the curable wax is performed by adding cooled water to the curable wax such that the curable wax becomes solid, isolating the solid curable wax by filtration, and drying the solid curable wax.

15. A method of manufacturing a radiation curable ink, the method comprising:
   forming a curable wax by a reaction between a wax having a transformable functional group and a curable compound, wherein the reaction occurs in the presence of an organic solvent in an amount of from about 12 wt % to about 36 wt %, and wherein after the forming of the curable wax, unreacted curable compound is removed by a process comprising:
   mixing water having temperature of more than about 85° C. into a mixture comprising the formed curable wax and unreacted curable compound,
   removing the unreacted curable compound from a waxy phase into a water phase, and
   removing the water phase and the unreacted curable compound, and mixing the curable wax with a curable monomer and a colorant to form a radiation curable ink.

16. The method of claim 15, wherein the wax having a transformable functional group is a hydroxyl-terminated polyethylene wax having the structure $CH_3-(CH_2)_n-CH_2OH$, wherein n=22-24.

17. A scalable process for the manufacture of a curable wax, the process comprising:
   mixing a wax having a transformable functional group and a curable compound in the presence of an organic solvent to form a reaction mixture;
   reacting the wax and the curable compound in the reaction mixture to form a curable wax;
   adding water to the reaction mixture;
   mixing the water and the reaction mixture;
   allowing the reaction mixture to separate into a waxy phase and a water phase; and
   removing the water phase, wherein
      the water has a temperature of more than about 85° C., and
      during the separation of the waxy phase and the water phase, unreacted curable compound separates into the water phase and is removed when the water phase is removed.

18. The scalable process of claim 17, wherein the adding, the mixing, and the separation, are performed at least 3 times.

* * * * *